United States Patent [19]

Goebbels

[11] 4,026,157

[45] May 31, 1977

[54] METHOD OF QUANTITATIVELY DETERMINING THE GRAIN SIZE OF SUBSTANCES

[75] Inventor: Klaus Goebbels, Saarbrucken, Germany

[73] Assignee: Fraunhofer-Gesellschaft zur Forderung der angewandten Forschug e.V., Munich, Germany

[22] Filed: Mar. 18, 1976

[21] Appl. No.: 667,940

[30] Foreign Application Priority Data

Mar. 18, 1975 Germany .......................... 2511750

[52] U.S. Cl. .............................. 73/432 PS; 73/67.6
[51] Int. Cl.² ................. G01N 15/02; G01N 29/00
[58] Field of Search ........... 73/432 PS, 61 R, 67.2, 73/67.6, 67.7

[56] References Cited

UNITED STATES PATENTS

| | | |
|---|---|---|
| 2,949,769 | 8/1960 | Heller ................................. 73/67.6 |
| 2,966,057 | 12/1960 | Heller ................................. 73/67.6 |
| 3,133,445 | 5/1964 | Richard .......................... 73/432 PS |
| 3,220,261 | 11/1965 | Kriebel .......................... 73/432 PS |
| 3,710,615 | 1/1973 | Johnson et al. ..................... 73/61 R |
| 3,779,070 | 12/1973 | Cushman et al. ............. 73/432 PS |
| 3,791,200 | 2/1974 | Hayre .......................... 73/61 R X |

Primary Examiner—Richard C. Queisser
Assistant Examiner—Joseph W. Roskos
Attorney, Agent, or Firm—John C. Smith, Jr.

[57] ABSTRACT

A method of quantitatively determining the grain size of substances comprises introducing ultrasound of two different frequencies and measuring the sonic pressure amplitudes of both frequencies, determining the attenuation coefficients from these measurements for both frequencies and finally calculating the value of $a_4$.

3 Claims, 2 Drawing Figures

METHOD OF QUANTITATIVELY DETERMINING THE GRAIN SIZE OF SUBSTANCES

BACKGROUND OF THE INVENTION

This invention relates to a method of quantitatively determining the grain size $d$ of substances having an ultra-sound attenuation coefficient $\alpha = \alpha_A + \alpha_S$, wherein the absorption coefficient $\alpha_A$ depends linearly upon the frequency $f$ of the ultrasound ($\alpha_A = a_1 f$) and the coefficient of scatter $\alpha_S$ is $H \cdot d^3 \cdot f^4 = a_4 f^4$ (for H = const (density, speed of sound and anisotropy)), by measuring the pressure amplitude $A_S(x)$ of the scattered sound as a function of the transit time of the sound through the specimen, and averaging over limited regions of structure by relative continuous or discontinuous movement between the source of the sound and the specimen.

Whereas the scatter of electromagnetic waves (X-rays, visible light, radar) has already found many uses in practice no advantage has as yet been taken of the possibility of utilizing the scatter of sound waves.

Ultrasonic pulses in steel are partly absorbed by the material and partly they excite the crystals (grains) of the structure to re-radiate detectable quantities of the sound (= scatter).

In the conventional technique of assessing the structure of a material by ultrasound the attenuation in planoparallel specimens due to absorption and scatter is measured and the result is evaluated. Scatter measurements call for a different experimental arrangement:

Ultrasonic bursts (frequencies between 5 and 25 MHz) are applied through a liquid entry path (e.g. through water) at an angle of incidence exceeding the angle of total reflection of the longitudinal wave, so that only the transversal wave is propagated through the material. The grains of the structure scatter the ultrasound in every direction but some of it is returned to the source (usually a piezoelectric material, such as quartz, lithium sulphate and so forth). The returning high frequency signals are amplified, converted to digital form in a high speed analog-to-digital converter (conversion rate about 100 MHz) and stored in a computer. Relative movement between the measuring head and the material (circular, elliptical or linear) yields different signals at different times from different parts of the structure. This averaging process is needed in order to eliminate signals caused by interference (from crystallites in particularly favorable or unfavorable locations. Rectification of the mean values provides a scatter amplitude distribution $A_S(x)$ as a function of the path length $x$ of the sound (calculated from velocity of the sound and its transit time).

For homogeneous workpieces $$A_S(x) = \text{const.} \cdot \sqrt{\alpha_S} \cdot e^{-\alpha x}$$

where $\alpha_S$ = coefficient of scatter $\alpha$ = coefficient of attenuation = $\alpha_A$ (absorption) + $\alpha_S$.

The constant contains all the parameters of external effects. The representation of $\log_e A_S(x)$ on a plotter indicates homogeneity by the linearity of $$\log_e A_S(x) \sim -\alpha_x.$$

Deviations from the straight line mean that there are inhomogeneities in the material.

The drawback of this procedure is that a calibrated specimen having a known type of structure is needed and this latter structure must be determined by other means. Hence the examination of different materials always requires the availability of corresponding calibrated specimens. (H. Koppelmann, Materialprufung 9 (1967), p.401, and J. Koppelmann, Materialprufung 14 (1972), p.156. Also B. Fay, Acoustica, vol. 28 (1973), p. 354).

SUMMARY OF THE INVENTION

It is the object of the present invention to provide a method which eliminates these drawbacks.

With reference to claim 1 the underlying theory may be briefly stated.

By logarithmation of the two functions $$A_{S1}(x) = \text{const.}_1 \cdot \sqrt{\alpha_{S1}} \cdot e^{-\alpha_1 x} \text{ and}$$

$$A_{S2}(x) = \text{const.}_2 \cdot \sqrt{\alpha_{S2}} \cdot e^{-\alpha_2 x}$$

which are obtained from the measurements for the two frequencies $f_1$ and $f_2$ (e.g. 5 and 10 MHz) the coefficients $$\alpha_1 = \alpha_{S1} + \alpha_{A1} \text{ and}$$

$$\alpha_2 = \alpha_{S2} + \alpha_{A2}$$

can be determined.

Since generally speaking grain size $d \ll$ wave length $\lambda$ $$\alpha_A = a_1 f \text{ and}$$

$$\alpha_S = a_4 f^4,$$

$$a_4 = \left( \alpha_2 - \alpha_1 \cdot \frac{f_2}{f_1} \right) / f_2 \cdot (f_2^3 - f_1^3)$$

can be calculated by the computer. The quantitative relationship $a_4 = d^3 \cdot H$ (density, sound velocities, anisotropy) is known and can be solved for $d$.

Claim 2 is based on the following considerations:

Assuming there are two specimens which may be referred to as $m$ and $n$ of the same material and the same surface finish, but differing in their structural states (e.g. due to different thermal treatments), then measurements with only one frequency will already provide $\alpha_{Si}$ and $d_i$ ($i = m, n$):

$$A_{Sm}(x) = \text{const.} \cdot \sqrt{\alpha_{Sm}} \cdot e^{-(\alpha_{Sm} + \alpha_A)x}; A_{Sm}(0) = \text{const.} \sqrt{\alpha_{Sm}}$$

$$A_{Sn}(x) = \text{const.} \cdot \sqrt{\alpha_{Sn}} \cdot e^{-(\alpha_{Sn} + \alpha_A)x}; A_{Sn}(0) = \text{const.} \sqrt{\alpha_{Sn}}$$

If the structural deviations are not too great (mainly this will relate to precipitations etc.)

$$\alpha_{Am} = \alpha_{An} = \alpha_A$$

will hold.

The combination of the two pairs of values gives ($\alpha_i = \alpha_{Si} + \alpha_A$, where $i = m, n$):

$$\alpha_{Sm} = (\alpha_m - \alpha_n) / \{1 - A_{Sm}^2(0)/A_{Sn}^2(0)\}$$

$$\alpha_{Sn} = (\alpha_n - \alpha_m) / \{1 - A_{Sn}^2(0)/A_{Sm}^2(0)\}$$

so that from $\alpha_{Si} = d_i^3 \cdot H$ the mean grain sizes $d_i$ can again be determined.

The required values of H must be taken from Bhatia's theory (Ultrasonic Absorption, Clarendon Press, Oxford 1967, p.278 et seq.) and individually programmed.

BRIEF DESCRIPTION OF THE DRAWING

In order that the invention may be more readily understood the general arrangement will now be purely illustratively described with reference to the accompanying drawing, in which.

DESCRIPTION OF THE PREFERRED EMBODIMENTS

By suitably chopping the sine wave of a high frequency generator 1 bursts of selectable length and repetition frequency (burst generator 2) are produced and applied through a power amplifier 3 to a test head 4 which is thereby induced to emit quasi-monochromatic ultrasound pulses.

Figure 1:
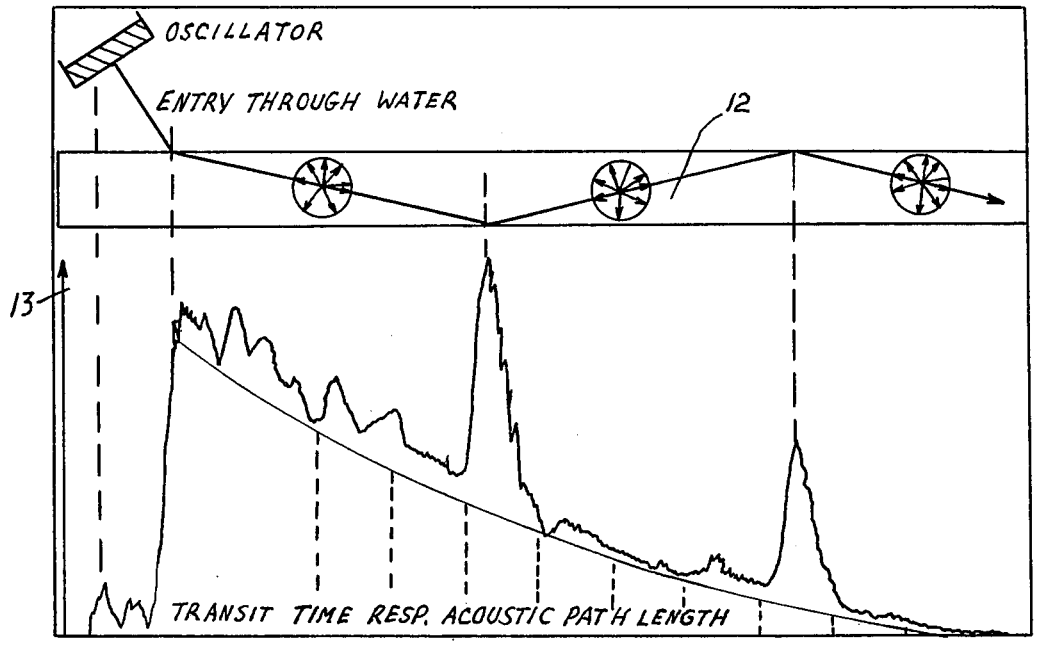
FIG. 1 is a diagrammatic representation of an arrangement for measuring the back scattered ultrasound.

At the end of an entry path through water (see FIG. 1) (water causes no scatter) reflected ultrasound (US) is measured first. Although the propagation axis of the sound to the surface is at an angle, a fraction of the intensity of the emitted pulse will nevertheless be perpendicularly incident and reflected at the surface. From this low amplitude 13 there is a rise to the scatter amplitude $A_S$ which returns from the surface.

The scatter amplitude will then usually (in the case of a homogeneous material) fall exponentially. If the specimen is thin (say 20mm and less) and attenuation slight (in a fine-grained structure and at low frequency) there will also be a superimposed scatter reflection from the undersurface of the specimen, and back and forth at the upper and undersurface until this is completely damped out. This and other sources of interference (for instance by surface waves) therefore make it advisable to evaluate a scatter measurement by plotting a bottom "limit curve." This will then provide the necessary data for a grain size determination (amplitude at surface; amplitude attenuation due to length of acoustic path). Relative motion between test head and specimen 12 during the measurement will average out over interference maxima and minima which are always present, so that a scatter amplitude curve will be obtained such as that shown in FIG. 1.

Figure 2:
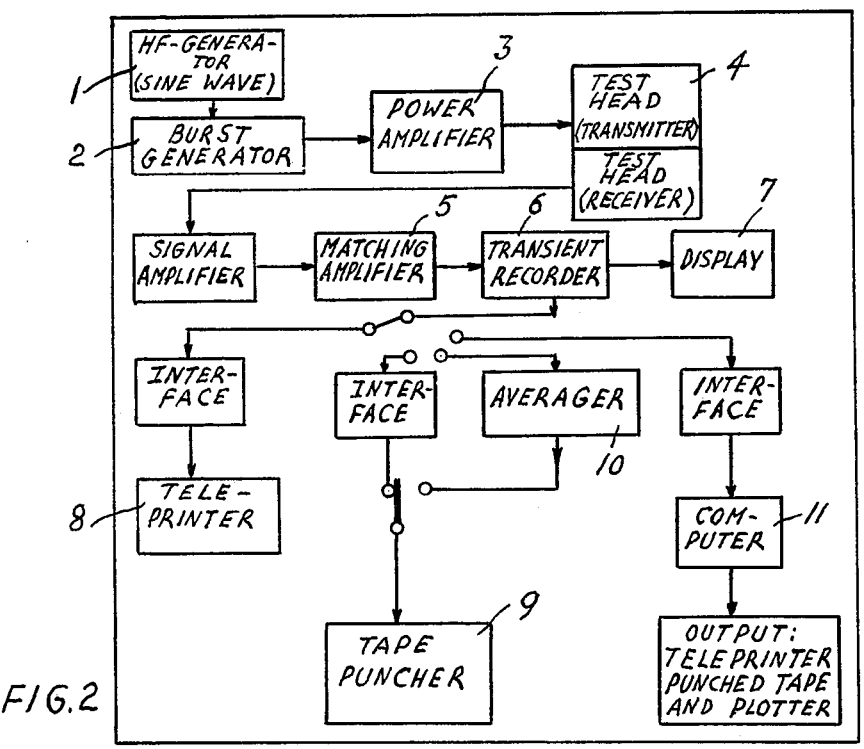
FIG. 2 is a block diagram of hardware for carrying out the scatter measurements.

After logarithmic amplification of the scatter signals that are received these are taken through a matching amplifier 5 for conversion to digital form to an analog-to-digital converter 6 (cf. FIG. 2). The measured signals can then be displayed by a display 7. Further processing is optional and the output may be teleprinted at 8 or applied to a tape puncher 9 or, for portable operation without a computer, any desired number of measurements may be applied to a signal averager 10 which permits the results of these measurements to be punched on tape, or a computer 11 may be on-line with the analog-to-digital computer for a programmed evaluation.

The invention may be embodied in other specific forms without departing from the spirit or essential characteristics thereof. The embodiments are therefore to be considered in all respects as illustrative and not restrictive.

What is claimed is:

1. A method of quantitatively determining the grain size $d$ of substances having an ultrasound attenuation coefficient $\alpha = \alpha_A + \alpha_S$, wherein the absorption coefficient $\alpha_A$ depends linearly upon the frequence $f$ of the ultrasound ($\alpha_A = a_1.f$) and the coefficient of scatter $\alpha_S$ is $H.D^3.f^4 = a_4.f^4$, H being a constant and based upon density, speed of sound and anisotrophy, by measuring the pressure amplitude $A_S(x)$ of the scattered sound as a function of the transit time of the sound through the specimen, and averaging over limited regions of structure by relative continuous or discontinuous movement between the source of the sound and the specimen, the invention consisting in introducing ultrasound of two different frequencies $f_1$ and $f_2$ and measuring the sonic pressure amplitudes of both frequencies $f_1$ and $f_2$, determining the attenuation coefficients $\alpha_1$ and $\alpha_2$ from these measurements for both frequencies $f_1$ and $f_2$ and finally calculating the value of $a_4$ from the equation $$a_4 = \left(\alpha_2 - \alpha_1 \cdot \frac{f_2}{f_1}\right) / f_2 \cdot (f_2^2 - f_1^2)$$

2. A method of quantitatively determining the grain size $d$ in substances having an ultrasound attenuation coefficient $\alpha = \alpha_A + \alpha_S$, wherein the absorption coefficient $\alpha_A$ can be regarded as being the same in two specimens and the coefficient of scatter $\alpha_S$ is $H.d^3.f^4 = a_4.f^4$, H being a constant based upon density, speed of sound and anisotrophy, by measuring the pressure amplitude $A_S(x)$ of the scattered sound as a function of the transit time of the sound wave through the specimen and averaging over limited regions of the structure by relative continuous or discontinuous motion between the source of the sound and the specimen, comprising introducing the same frequency into the two specimens, identified by $m$ and $n$, of the same material but having different structures, measuring the scatter amplitudes $A_{Si}(0)$ and the respective sonic pressure amplitudes $A_{Si}(x)$ ($i = m, n$) at the surfaces of both specimens and directly determining the coefficients of scatter $\alpha_{Sm}$ and $\alpha_{Sn}$ from the measured attenuation coefficients $\alpha_m$ and $\alpha_n$ by calculation from $$\alpha_{Sm} = (\alpha_m - \alpha_n) / \{1 - A_{Sn}^2(0)/A_{Sm}^2(0)\} \text{ and}$$

$$\alpha_{Sn} = (\alpha_n - \alpha_M) / \{1 - A_{Sm}^2(0)/A_{Sn}^2(0)\}$$

3. The method defined in claim 1 comprising the choice of a frequency so that $d/\lambda = 0.1 - 0.5$.